United States Patent [19]

Kao

[11] 4,207,419
[45] Jun. 10, 1980

[54] PROSTAGLANDIN DERIVATIVES

[75] Inventor: Wenling Kao, King of Prussia, Pa.

[73] Assignee: American Home Products Corporation, New York, N.Y.

[21] Appl. No.: 759,314

[22] Filed: Jan. 13, 1977

[51] Int. Cl.$^2$ .......................................... C07C 177/00
[52] U.S. Cl. ......................................... 560/53; 562/463
[58] Field of Search ........................... 560/53; 562/463

[56] References Cited

U.S. PATENT DOCUMENTS

| 3,971,826 | 7/1976 | Hess | 260/520 B |
|---|---|---|---|
| 4,029,693 | 6/1977 | Bundy et al. | 560/53 |

OTHER PUBLICATIONS

67250X/36 Derwent Abstract.
46023U-B Derwent Abstract.

*Primary Examiner*—Paul J. Killos
*Attorney, Agent, or Firm*—Arthur G. Seifert

[57] ABSTRACT

Derivatives of 11-deoxy-PGE$_2$ are prepared. These new compounds not heretofore found in nature possess various pharmacological activities, one of which is bronchodilation.

6 Claims, 1 Drawing Figure

PROSTAGLANDIN DERIVATIVES

BACKGROUND OF THE INVENTION

The prostaglandins are a group of hormone-like substances which may be viewed as derivatives of prostanoic acid. Several prostaglandins are found widely distributed in mammalian tissue and have been isolated from this source. These prostaglandins have been shown to possess a variety of biological properties such as bronchodilation and the ability to reduce gastric secretion.

The present invention concerns prostaglandin $E_2$ and certain reduced prostaglandin $E_2$ derivatives in which the 9-position (using the prostanoic acid numbering system) remains intact as a carbonyl group; the 11-position is a methylene group, i.e. the 11-hydroxyl group normally present in $PGE_2$ has been removed and is replaced with hydrogen; the 16-position bears two methyl groups; and the normally present 17-20 carbon atoms have been removed and replaced with either a phenyl or benzyl group.

SUMMARY OF THE INVENTION

The invention sought to be patented in a first composition aspect resides in the concept of a chemical compound of the structure:

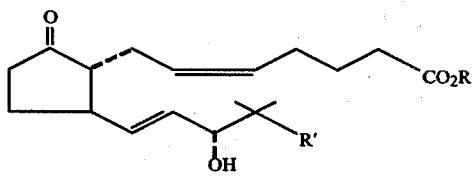

wherein R is alkyl of from 1 to 6 carbon atoms, and $R^1$ is benzyl or phenyl.

The tangible embodiments of the first composition aspect of the invention possess the inherent general physical properties of being clear to yellow oils, are substantially insoluble in water and are generally soluble in organic solvents such as ethyl acetate and ether. Examination of compounds produced according to the hereinafter described process reveals, upon infrared and nuclear magnetic resonance spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the first composition aspect of the invention possess the inherent applied use characteristic of being intermediates for the synthesis of the embodiments of the third and fourth composition aspects of the invention.

The invention sought to be patented in a second composition aspect resides in the concept of a chemical compound of the structure:

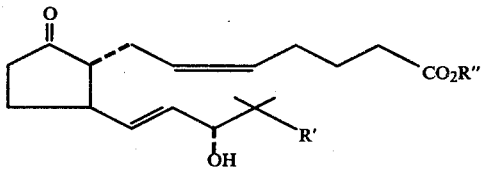

wherein $R^1$ is phenyl or benzyl and R" is hydrogen, an alkali metal cation, or a pharmacologically acceptable cation derived from ammonia or a basic amine.

The tangible embodiments of the second composition aspect of the invention possess the inherent general physical properties of being clear to yellow oils, and when R" is hydrogen, they are substantially insoluble in water and are generally soluble in organic solvents such as ethyl acetate and ether. Examination of compounds produced according to the hereinafter described process reveals, upon infrared and nuclear magnetic resonance spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the second composition aspect of the invention possess the inherent applied use characteristic of being intermediates for the synthesis of the embodiments of the third and fourth composition aspects of the invention. In addition, the embodiment wherein $R^1$ is phenyl and R" is hydrogen exerts hypotensive effects upon administration to warm-blooded animals as evidenced by pharmacological evaluation according to standard test procedures.

The invention sought to be patented in a third composition aspect resides in the concept of a chemical compound of the structure:

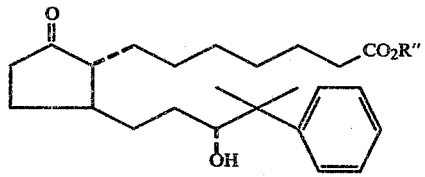

wherein R" is hydrogen, an alkali metal cation, or a pharmacologically acceptable cation derived from ammonia or a basic amine.

The tangible embodiments of the third composition aspect of the invention possess the inherent general physical properties of being clear to yellow oils, and when R" is hydrogen, are subtantially insoluble in water and generally soluble in organic solvents such as ethyl acetate and ether. Examination of compounds produced according to the hereinafter described process reveals, upon infrared and nuclear magnetic resonance spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the third composition aspect of the invention possess the inherent applied use characteristic of exerting hypotensive effects upon administration to warm-blooded animals as evidenced by pharmacological evaluation according to standard test procedures.

The invention sought to be patented in a fourth composition aspect resides in the concept of a chemical compound of the structure:

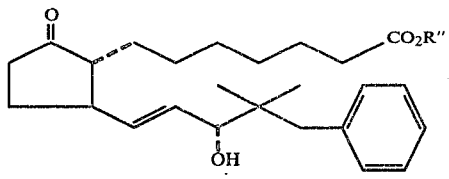

wherein R″ is hydrogen, an alkali metal cation, or a pharmacologically acceptable cation derived from ammonia or a basic amine.

The tangible embodiments of the fourth composition aspect of the invention possess the inherent general physical properties of being clear to yellow oils, and when R″ is hydrogen, are substantially insoluble in water and generally soluble in organic solvents such as ethyl acetate and ether. Examination of compounds produced according to the hereinafter described process reveals, upon infrared and nuclear magnetic resonance spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the fourth composition aspect of the invention possess the inherent applied use characteristic of exerting bronchodilating effects upon administration to warm-blooded animals as evidenced by pharmacological evaluation according to standard test procedures.

DESCRIPTION OF THE PREFERRED EMBODIMENTS

Figure 1:
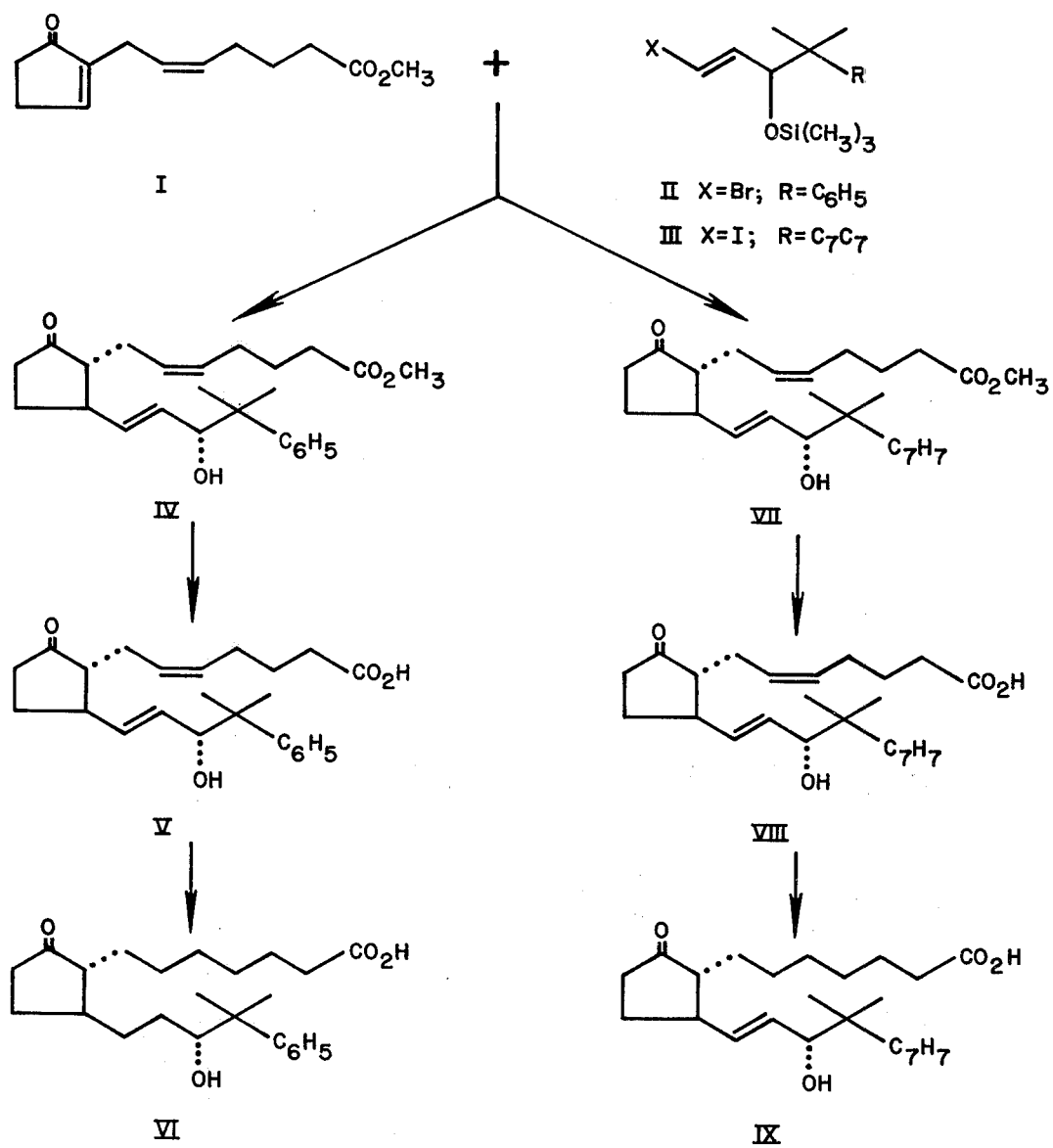

In describing the synthesis of the compositions of the invention, reference will be made to FIGURE I, wherein is illustrated the preparation of specific embodiments of the invention, and wherein the formulae representing the various aspects of the invention are assigned Roman numerals for purposes of identification. Additionally, in order to designate the stereochemistry of various substituents on the prostaglandin skeleton, different types of lines are utilized when representing the bonds of said substituents. Thus, with reference to the plane of paper, when a dashed line (--) is used, the substituent will be understood to be in the α (down) configuration. The formulae in FIGURE I are either free carboxylic acids or esters and it will be obvious to those skilled in the art that the esters may be converted to their respective free acids by, for example, hydrolysis with dilute base and the free acids may readily be esterified as for example, with diazomethane, or with an alkanol and the proper catalyst or the free acids may be converted to an alkali metal or basic amine salt. For reasons of convenience the shorthand notations $C_6H_5$ and $C_7H_7$ are utilized in the structures to denote, respectively, the phenyl and benzyl groups. Finally, the use of specific embodiments in FIGURE I to illustrate the invention is merely descriptive and is not intended to delimit the scope of the invention.

Referring now to FIGURE I, the starting material of formula I may be obtained as described by Bagil, J., and Bogri, T., Tetrahedron Letters, p. 3815 (1972), and the starting materials of formulae II and III may be prepared as described in the examples infra, or if desired, by obvious variations thereof. It will be obvious to those skilled in the art that condensation of I with II will produce the intermediates and products bearing a phenyl group at the 16-position (i.e. compounds IV-VI) and that condensation of I with III will produce the intermediates and products bearing a benzyl group at the 16-position (i.e. compounds VII-IX). It will also be obvious to those skilled in the art that these condensations will produce products which are C-15 isomeric mixtures; these isomers are readily separated by, for example, chromatographic means. The 15α isomers are contemplated by the instant invention.

The 1,4-conjugate addition of I and II is carried out by the procedure described by Corey, E. J., J. Am. Chem. Soc., 94, 7210 (1972), and after chromatographic separation of the product mixture, IV is obtained. The ester function of IV is hydrolyzed with, for example, dilute sodium hydroxide/THF solution producing V. The double bonds of V are next reduced with $H_2$ at atmospheric pressure using tris(triphenylphosphine)rhodium (I) chloride as catalyst producing VI.

Alternatively, compound I may be condensed with III using the procedure described by E. J. Corey, supra, and after chromatographic separation of the C-15 isomeric product mixture, VII is obtained. The ester function of VII may be hydrolyzed with, for example, dilute sodium hydroxide/THF solution producing VIII. The 5,6 double bond of VIII is selectively reduced with $H_2$ at atmospheric pressure using tris(triphenylphospine)rhodium (I) chloride as catalyst by stopping the reduction when 1 equivalent of $H_2$ has been absorbed.

When used herein and in the appended claims, the term "alkali metal" includes, for example, sodium, potassium, lithium, and the like. A "pharmacologically acceptable cation derived from ammonia or a basic amine" contemplates the positively charged ammonium ion and analogous ions derived from organic nitrogenous bases strong enough to form such cations. Bases useful for the purpose of forming pharmacologically acceptable non-toxic addition salts of such compounds containing free carboxyl groups form a class whose limits are readily understood by those skilled in the art. Merely for illustration, they can be said to comprise, in cationic form, those of the formula:

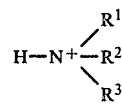

wherein $R^1$, $R^2$, and $R^3$, independently, are hydrogen, alkyl of from 1 to about 6 carbon atoms, cycloalkyl of from about 3 to about 6 carbon atoms, monocarbocyclicaryl of about 6 carbon atoms, monocarbocyclicarylalkyl of from about 7 to about 11 carbon atoms, hydroxyalkyl of from about 1 to about 3 carbon atoms, or monocarbocyclicarylhydroxyalkyl of from about 7 to about 15 carbon atoms or, when taken together with the nitrogen atom to which they are attached, any two of $R^1$, $R^2$, and $R^3$ form part of a 5 to 6-membered heterocyclic ring containing carbon, hydrogen, oxygen, nitrogen, said heterocyclic rings and said monocarbocyclicaryl groups being unsubstituted or mono- or dialkyl substituted, said alkyl groups containing from about 1 to about 6 carbon atoms. Illustrative therefore of R groups comprising pharmacologically acceptable cations derived from ammonia or a basic amine are ammonium, mono-, di-, and tri-methylammonium, mono-, di-, and triethylammonium, mono-, di-, and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butylpiperidinium, 2-methylpiperidinium, 1-ethyl-2-methylpiperidinium, mono-, di- and triethanolammonium, ethyldiethanolammonium, n-butylmonoethanolammonium, tris-(hydroxymethyl)-methylammonium, phenylmonoethanolammonium, and the like.

The following examples further illustrate the best mode contemplated by the inventor for the practice of the invention.

EXAMPLE 1

PREPARATION OF 1-BROMO-4-METHYL-4-PHENYL-3-TRIMETHYLSILYLOXY-TRANS-1-PENTENE II

2-Methyl-3-Phenyl-2,3-butanediol

Ref: Bull. Soc. Chim. Fr., 1115 (1970)

A solution of 20.4 g. of 3-hydroxy-3-methyl-2-butanone (commerically available) in 60 ml. of dry tetrahydrofuran was treated at 0° C. with 200 ml. of 3M phenyl magnesium bromide and stirred at 50° C. under $N_2$ for two hours. The mixture was added to aqueous ammonium chloride solution, acidified at 0° C. with conc. HCl and extracted with ether. After washing with water and drying with magnesium sulfate, the extract was concentrated to give crystalline material. Recrystallization from ether-pentane afforded 21.0 g. of the title product, m.p. 81°-83°, $\lambda_{max}^{KBr}$ 3.0, 3.35, 6.85, 7.15, 7.25, 8.6, 9.0, 9.35, 9.6, 10.3, 10.8, 11.5, 12,22, 13.05, and 14.15μ.

NMR Analysis: 1.05 and 1.22 (each s, 3,

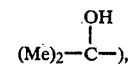

1.65

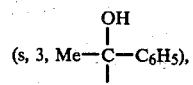

2.20 and 2.79 (each s, 1, OH), 7.30 (m, 5, —$C_6H_5$) ppm.

Mass Spectral Analysis: M+—$H_2O$ at m/e 162 (theory 162).

3-Methyl-3-Phenyl-2-Butanone

Ref: C. R. Acad. Sci. Ser., B277,727 (1973)

A solution of 18.0 g. of 2-methyl-3-phenyl-2,3-butanediol in tetrahydrofuran was treated at 40° C. with an ice-cooled solution of 200 ml. of 50% $H_2SO_4$. After stirring at 25° C. for 20 hours, the mixture was treated with crushed ice and extracted with ether. The extract was neutralized with sodium bicarbonate solution, washed with brine and dried with magnesium sulfate. The solvent was evaporated and the residue was distilled under reduced pressure to afford 15.0 g. of the title product as an oil, B.P. 70°-71° 1.5 mm. [Lit. 97°-98°/11 mm., Bull. Soc. Chim. France, 3, 239 (1936)]. $\lambda_{max}^{film}$ 3.45, 5.82, 6.67, 7.39, 8.88, 9.27, 12.64, 13.10 and 14.25 μ.

NMR Analysis: δ1.50

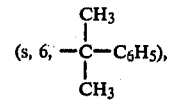

1.94

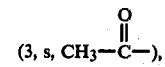

(s, 5, aromatic H) ppm.

Mass Spectral Analysis: M+ at m/e 162 (theory 162).

4-Methyl-3-Oxo-4-Phenylpentanal

A mixture of 8.8 g. of 50% NaH oil dispersion in 150 ml. of dry benzene was treated at 25° C. with 13.6 g. of ethylformate in 20 ml. of dry benzene under $N_2$. Over a period of a half hour, 14.9 g. of 3-methyl-3-phenyl-2-butanone in 80 ml. of dry benzene was added at 0° C. After stirring at 40° C. for 4 hours, the mixture was diluted with 250 ml. of ether, treated with ice and acidified with hydrochloric acid. The acidic solution ws extracted with ether and the ether extract was washed with brine, sodiuim bicarbonate solution, washed again with brine and dried. The solvent was evaporated and the residue was distilled under reduced pressure to afford 14.8 g. of the title product as an oil, B. P. 83°-84°/0.2 mm., $\lambda_{max}^{film}$ 3.5 (broad) 5.75, 5.90, 6.12, 6.30, 6.70, 6.80, 6.95, 7.31, 7.94, 8.18, 9,38, 12,60, 13.05 and 14.28 μ.

NMR Analysis: δ1.53 (s, 6, $CH_3$), 5.33

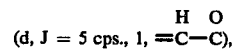

7.33 (s, 5, aromatic H), 7.65

Mass Spectral Analysis: M+ at m/e 190 (theory 190).

1-Chloro-4-Methyl-4-Phenyl-trans-1-Penten-3-One

A solution of 14 g. of 4-methyl-3-oxo-4-phenylpentanal in 50 ml. of dry benzene. After refluxing for 3½ hours, the solvent was evaporated. The residue was distilled under reduced pressure to afford 12.5 g. of the title product as a colorless oil, B. P. 88°-89°/0.3 mm. $\lambda_{max}^{film}$ 3.34, 5.85, 6.25, 6.62, 6.75, 6.88, 7.18, 7.27, 7.70, 8.00, 9.22, 9.42, 9.64, 9.95, 10.60, 11.10, 12.40, 13.02, 13.55 and 14.22 μ.

Mass Spectral Analysis: M+ at m/e 209 (theory 209).

UV Spectrum: $\lambda_{max}^{EtOH}$ 235 mμ (ε 14,500).

1-Bromo-4-Methyl-4-Phenyl-trans-1-Penten-3-One

A solution of 14 g. of 1-chloro-4-methyl-4- phenyl-1-trans-1-penten-3-one in 90 ml. of dimethoxyethane was treated with 24 g. of lithium bromide and refluxed for 24 hours. The mixture was diluted at 0° C. with ether, washed with brine, dried with $MgSO_4$ and evaporated to dryness. The residue was redissolved in dimethoxyethane, treated with lithium bromide and refluxed for an additional 24 hours. After the exact same process was repeated thrice and the crude product was chromatographed on silica gel. Elution with 5% ethyl acetate in hexane afforded 8.9 g. of the title produce as a yellow oil, $\lambda_{max}^{film}$ 3.4, 5.88, 6.32, 6.66, 6.78, 6.88, 7.70, 9.25, 9.48, 9.98, 10.64, 12.80, 13.10 and 14.25 μ.

NMR Analysis: δ 1.48 (s, 6, —CH₃), 6.56

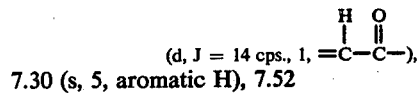

(d, J = 14 cps., 1, =C—C—), 7.30 (s, 5, aromatic H), 7.52

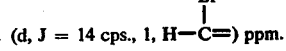

(d, J = 14 cps., 1, H—C=) ppm.

Mass Spectral Analysis: MH+ at m/e 209 (theory 209).

1-Bromo-4-Methyl-4-Phenyl-trans-1-Penten-3-ol

An ice-cold solution of 7.8 g. of 1-bromo-4-methyl-4-phenyl-trans-1-penten-3-one in 100 ml. of methanol was treated with 1.4 g. of sodium borohydride and stirred at 0° for one hour. The solvent was evaporated and the residue was dissolved in water then extracted with ether. The ether extract was dried with MgSO₄ and evaporated to afford 8.0 g. of the title product as a colorless oil, $\lambda_{max}^{film}$ 2.95, 3.4, 6.12, 6.20, 6.62, 6.88, 7.18, 7.28, 7.82, 9.30, 9.68, 10.00, 10.55, 12.95, 13.45 and 14.24 μ.

NMR Analysis: δ 1.30

(s, 6, —CH₃), 1.60 (d, 1.60, 1, OH), 4.12

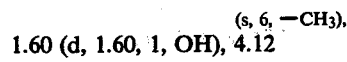

(t, 1, —C—OH), 6.21 (m, 2, olefinic H), 7.33 (s, 5, aromatic H) ppm.

Mass Spectral Analysis: M+ at m/e 255 (theory 255).

1-Bromo-4-Methyl-4-Phenyl-3-Trimethylsilyloxy-trans-1-Pentene

A solution of 7.8 g. of 1-bromo-4-methyl-4-phenyl-trans-1-pentene-3-ol in a mixture of 45 ml. of ether and 15 ml. of tetrahydrofuran was treated with 4.2 g. of imidazol under N₂. After imidazol dissolved completely, the solution was treated at 0° with 5 ml. of trimethylsilyl chloride and stirred for one hour. The solvents were evaporated at 25° and the residue was diluted with n-pentane. After passing through an alumina column, the n-pentane filtrate was evaporated at 25° to afford 9.0 g. of the title product as a colorless liquid, $\lambda_{max}^{film}$ 3.45, 6.15, 6.65, 6.90, 7.20, 7.30, 7.98, 8.90, 9.10, 9.22, 10.60, 11.30, 11.85, 13.14 and 14.25 μ.

NMR Analysis: δ 0.06 (s, 9, CH₃—Si—), 4.09 (m, 1, H—C—OTMS), 6.02 (m, 2, olefinic H) and 7.30 (s, 5, aromatic H) ppm.

EXAMPLE 2

Preparation of 1-Iodo-4,4-Dimethyl-5-Phenyl-3-Trimethylsilyloxy-trans-1-Pentane III

2,3-Dimethyl-4-Phenyl-2,3-Butanediol

A solution of 41 g. of 3-hydroxy-3-methyl-2-butanone in 300 ml. of dry tetrahydrofuran was treated at −10° under nitrogen with 500 ml. of 2M benzyl magnesium chloride and stirred at 25° C. for 20 hours. An aqueous ammonium chloride solution was added at 0° and the mixture was acidified at 0° with concentrated hydrochloric acid and extracted with ethyl acetate. The extract was evaporated and the residue chromatographed on silica gel. Elution with 20% ethyl acetate in hexane followed by recrystallization from the same solvent afforded 38 g. of the title product, m.p. 72°-74°, $\lambda_{max}^{KBr}$ 2.95, 3.35, 6.2, 6.63, 6.82, 7.23, 7.45, 7.65, 8.32, 8.70, 9.13, 10.58, 11.0, 11.40, 12.30, 12.97 and 14.06 μ.

3,3-Dimethyl-4-Phenyl-2-Butanone

Ref: Bull. Chim. Soc. Fr., 912 (1970)

A solution of 27 g. of 2,3-dimethyl-4-phenyl-2,3-butanediol in 5 ml. of tetrahydrofuran was treated at 0° with 180 ml. of 60% H₂SO₄ and stirred at 25° for 3 hours. The mixture was cooled to 0° and extracted with ether. The extract was neutralized with a sodium bicarbonate solution, washed with brine and dried. Solvent was evaporated and the residue was distilled under reduced pressure to afford a colorless oil, B.P. 82°-84°/0.1 mm. $\lambda_{max}^{film}$ 3.4, 5.82, 6.2, 6.65, 6.78, 6.85, 7.35, 8.94, 13.28 and 14.14 μ.

NMR Analysis: δ1.10

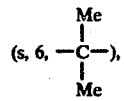

2.10

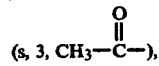

2.82 (s,2, benzylic H), 7.24 (m, 5, aromatic H) ppm.

Mass Spectral Analysis: M+ at m/e 176 (theory 176).

4,4-Dimethyl-3-Oxo-5-Phenylpantanal

A mixture of 10.6 g. of 50% NaH oil dispersion in 100 ml. of dry benzene was treated at 25° with 17.0 g. of ethylformate in 50 ml. of dry benzene under N₂. Over a period of a half hour, 17.6 g. of 3,3-dimethyl-4-phenyl-2-butanone in 50 ml. of dry benzene was added at 25° and stirred for 20 hours under nitrogen. The mixture was diluted at 0° with water, acidified with hydrochloric acid and extracted with ether. The extract was washed with brine, dried with magnesium sulfate, and evaporated to dryness. Distillation under reduced pressure afforded 18 g. of the title product as a colorless oil, B.P. 92°-94°/0.1 mm., $\lambda_{max}^{film}$ 3.5 (broad), 6.12, 6.27, 6.89, 7.34, 8.0, 9.35, 12.80, 13.50 and 14.20 μ.

NMR Analysis: δ1.13

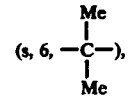

2.85 (s, 2, benzylic H), 5.60

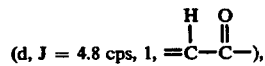

7.22 (m, 5, aromatic H), 8.11

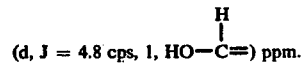

UV Spectrum: $\lambda_{max}^{EtOH}$ 270 mμ (ε 4,7000).

1-Chloro-4,4-Dimethyl-5-Phenyl-trans-1-Penten-3-One

A solution of 6.6 g. of 4,4-dimethyl-3-oxo-5-phenylpentanal in 25 ml. of dry benzene was treated with 4.7 g. of thionyl chloride and refluxed for 2½ hours. Solvent was evaporated and the residue was distilled under reduced pressure to afford 5.8 g. of the title product as a colorless oil, B.P. 86°–90°/0.1 mm. $\lambda_{max}^{film}$ 3.45, 5.92, 6.32, 6.70, 6.82, 9.30, 9.48, 10.65, 11.95, 12.50, 13.0, 13.54 and 14.23 μ.

NMR Analysis: δ1.12

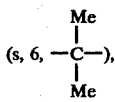

2.84 (s, 2, benzylic H), 6.92

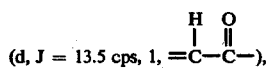

7.23 (m, 5, aromatic H), and 7.38

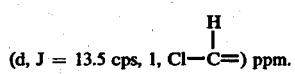

Mass Spectral Analysis: M+ at m/e 222 (theory 222).
UV Spectrum: $\lambda_{max}^{EtOH}$ 234 mμ (ε 11,360).

1-Iodo-4,4-Dimethyl-5-Phenyl-trans-1-Penten-3-One

A solution of 5.7 g. of 1-chloro-4,4-dimethyl-5-phenyl-trans-1-penten-3-one in 30 ml. of dry acetone was treated with 4.3 g. of sodium iodide and refluxed under nitrogen for 20 hours. The mixture was cooled, filtered and evaporated. The residue was dissolved in ether, washed with water and dried with magnesium sulfate. Evaporation of the solvent gave 7.6 g. of the title product as an oil, $\lambda_{max}^{film}$ 3.5, 5.91, 6.4, 6.68, 6.80, 7.7, 9.3, 9.56, 10.0, 10.58, 13.4 and 14.2 μ.

NMR Analysis: δ 1.13

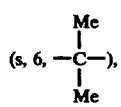

2.84 (s, 2, benzylic H), 7.23 (m, 5, aromatic H), 7.54

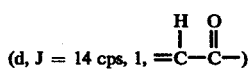

and 7.94

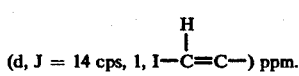

Mass Spectral Analysis: M+ at m/e 314 (theory 314).
UV Spectrum: $\lambda_{max}^{EtOH}$ 260 mμ (ε 7,800).

1-Iodo-4,4-Dimethyl-5-Phenyl-trans-Penten-3-ol

An ice-cold solution of 7.5 g. of 1-iodo-4,4-dimethyl-5-phenyl-trans-1-penten-3-one in 150 ml. of methanol was treated with 0.89 g. of sodium borohydride and stirred at 0° for 1½ hours. The solvent was evaporated and the residue was dissolved in water and then extracted with ether. The ether was dried and evaporated to afford 7.5 g. of the title product as an oil, $\lambda_{max}^{EtOH}$ 3.0, 3.45, 6.23, 6.70, 6.82, 6.90, 7.23, 7.34, 7.87, 8.55, 9.28, 9.71, 10.0, 10.56, 13.04, 13.6 and 14.2μ.

NMR Analysis: δ 0.83 and 0.90

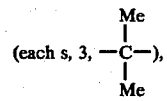

1.59 (s, 1, OH), 2.47 and 2.78 (each d, J=13 cps, 1, benzylic H), 3.81

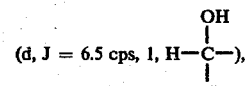

6.20–6.92 (m, 2, olefinic H), and 7.25 (s, 5, aromatic H) ppm.

1-Iodo-4,4-Dimethyl-5-Phenyl-3-Trimethyl-Silyloxy-trans-1-Pentene

A solution of 7.3 g. of 1-iodo-4,4-dimethyl-5-phenyl-trans-1-penten-3-ol and 1.5 g. of imidazol in 12 ml. of dry tetrahydrofuran was treated at 25° with 9 ml. of hexamethyldisilylazane and 0.9 ml. of trimethylchlorosilane. After stirring under nitrogen for one hour, the solvent was removed at 25° and the residue was diluted with n-pentane. Passing through alumina column, n-pentane filtrate was evaporated at 25° to afford 9.2 g. of the title product as a liquid, $\lambda_{max}^{film}$ 3.4, 6.22, 6.68, 6.7, 6.87, 7.2, 7.32, 7.98, 8.58, 9.3, 10.48, 11.35, 11.81, 13.3, 13.82 and 14.2μ.

NMR Analysis: δ 0.12 (s, 9, CH₃—SI—), 0.75 and 0.78

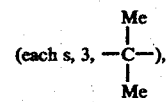

2.55 (s, 2, benzylic H), 3.75

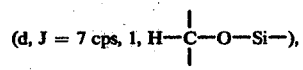

6.08–6.87 (m, 2, olefinic H) and 7.23 (s, 5, aromatic H) ppm.

Mass Spectral Analysis: M+ at m/e 388 (theory 388).

EXAMPLE 3 dl-7-{2β-[(3S)-3-Hydroxy-4,4-Dimethyl-4-Phenyl-trans-1-Butenyl]-5-Oxo-1α-Cyclopentyl}-cis-5-Heptenoic Acid, Methyl Ester 15-epi-IV and dl-7-{2β[(3R)-3-Hydroxy-4,4-Dimethyl-4-Phenyl-trans-1-Butenyl]-5-Oxo-1α-Cyclopentyl}-cis-5-Heptenoic Acid, Methyl Ester IV A solution of 9.0 g. of 1-bromo-4-methyl-4-phenyl-3-trimethylsilyloxy-trans-1-pentene in 80 ml. of ether under nitrogen was cooled in a dry-ice acetone bath and treated with 56 ml. of 1.24 M t-butyl lithium in pentane. After stirring at −78° for 2 hours, a freshly prepared solution of 9.0 g. of hexamethylphosphorous-triamide and 3.64 g. of n-propylethynyl copper in 30 ml. of ether was added to the reaction mixture and stirring continued for ½ hour under nitrogen at −78°. A solution of 1.8 g. of 7-(5-oxo-1-cyclopentenyl)-cis-5-heptenoic acid, methyl ester in 20 ml. of ether was then added and the mixture stirred at −78° for ½ hour, at −10° for one hour and at 0° for ½ hour. The reaction mixture was added to a saturated ammonium sulfate solution, extracted with ether and the extract washed with 10% sulfuric acid, filtered through Celite, washed with brine and dried. Evaporation of the solvent gave a residue as an oil. The crude oil was treated with a mixture of 20 ml. of tetrahydrofuran, 20 ml. of water and 40 ml. of acetic acid, and stirred at 25° for one hour. After evaporation of the solvent, the residue chromatographed on silica gel. Elution with 18% ethyl acetate in hexane afforded 0.51 g. of the first title product as a colorless oil, $\lambda_{max}^{film}$ 2.95, 3.45, 5.72, 6.20, 6.61, 6.80, 7.28, 8.60, 9.25, 9.65, 10.22, 12.98 and 14.2μ.

NMR Analysis: δ 1.32

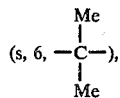

1.87 (s, 1, OH), 3.70 (s, 3, COOMe), 4.14

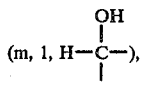

5.47 (m, 4, olefinic H) and 7.40 (s, 5, aromatic H) ppm.

Mass Spectral Analysis: M+-H₂O at m/e 380 (theory 380).

Continuing elution with 18% ethyl acetate in hexane afforded 0.4 g. of the second title product as a colorless oil, $\lambda_{max}^{film}$ 2.95, 3.45, 5.72, 6.20, 6.62, 6.90, 7.28, 8.60, 9.66, 10.25, 13.0 and 14.2μ.

NMR Analysis: δ 1.35

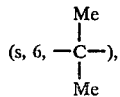

1.81 (s, 1, OH), 3.68 (s, 3, COOMe), 4.17

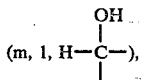

5.46 (m, 4, olefinic H) and 7.37 (s, 5, aromatic H) ppm.

Mass Spectral Analysis: M+-H₂O at m/e 380 (theory 380).

EXAMPLE 4 dl-7-{2β-[(3R)-3-Hydroxy-4,4-Dimethyl-4-Phenyl-trans-1-Butenyl]-5-Oxo-1α-Cyclopentyl}-cis-5-Heptenoic Acid V A solution of 0.3 g. of dl-7-{2β-[(3R)-3-hydroxy-4,4-dimethyl-4-phenyl-trans-1-butenyl]-5-oxo-1α-cyclopentyl}-cis-5-heptenoic acid, methyl ester in 5 ml. of tetrahydrofuran and 10 ml. of 2N sodium hydroxide solution was stirred at 25° for 20 hours. The mixture was acidified with acetic acid, diluted with brine and extracted with ether. After washing and drying, the solvent was evaporated and the residue chromatographed on silica gel. Elution with 25% ethyl acetate in hexane afforded 0.25 g. of the title product as a colorless oil, $\lambda_{max}^{film}$ 2.95, 3.48, 5.80, 6.20, 6.62, 6.90, 7.10, 7.30, 8.20, 8.60, 9.70, 10.20, 13.0 and 14.20μ.

NMR Analysis: δ 1.35

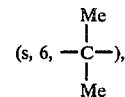

4.20

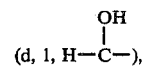

5.5 (m, 4, olefinic H), 6.20 (s, 2, OH), and 7.38 (s, 5, aromatic H) ppm.

Mass Spectral Analysis: M+-C₉H₁₁ at m/e 265 (theory 265).

EXAMPLE 5 dl-2β-[(3R)-3-Hydroxy-4,4-Dimethyl-4-Phenyl-1-Butyl]-5-Oxo-1α-Cyclopentane Heptanoic Acid VI A solution of 0.17 g. of 7-{2β-[(3R)-3-hydroxy-4,4-dimethyl-4-phenyl-trans-1-butenyl]-5-oxo-1α-cyclopentyl}-cis-5-heptenoic acid and 0.10 g. of tris(triphenylphosphine)rhodium (I) chloride in 30 ml. of a mixture of ethanol-benzene (1:1) was hydrogenated at 25° and atmospheric pressure until 2 equivalents of hydrogen were absorbed. After filtering, the solution was evaporated and the residue chromatographed on silica gel. Elution with 25% ethyl acetate in hexane afforded 0.10 g. of the title product as an oil, $\lambda_{max}^{film}$ 3.0 (shoulder) 3.5, 5.75, 6.25, 6.18, 6.92, 7.10, 8.70, 9.0, 13.05 and 14.23μ.

NMR Analysis: δ 3.56 (m, 1, 15-H), 5.93 (s, 2, OH), 7.29 (s, 5, aromatic H) ppm.

Mass Spectral Analysis: M+-[C₉H₁₁+2H₂O] at m/e 233.1557 (theory 233.1557).

EXAMPLE 6 dl-7-{2β-[(3S)-3-Hydroxy-4,4-Dimethyl-5-Phenyl-trans-1-Pentenyl]-5-Oxo-1α-Cyclopentyl}-cis-5-Heptenoic Acid, Methyl Ester 15-epi-VII and dl-7-{2β-[(3R)-3-Hydroxy-4,4-Dimethyl-5-Phenyl-trans-1-Pentyl]-5-Oxo-1α-Cyclopentyl}-cis-5-Heptenoic Acid, Methyl Ester VII A solution of 8.6 g. of 1-iodo-4,4-dimethyl-5-phenyl-3-trimethylsilyloxy-trans-1-pentene in 50 ml. of ether under nitrogen was cooled in a dry ice-acetone bath and treated with 36 ml. of 1.24 M t-butyl lithium in pentane. After stirring at −78° for 2 hours, a freshly prepared solution of 7.2 g. of hexamethylphosphorous triamide and 2.9 g. of n-propylethynyl copper in 30 ml. of ether was added to the reaction mixture and stirring continued for ½ hour under nitrogen at −78°. A solution of 3.5 g. of 7-(5-oxo-1-cyclopentenyl)-cis-5-heptenoic acid, methyl ester in 10 ml. of ether was then added and the mixture stirred at −78° for one hour, at −15° for one hour and at 0° for one hour. The reaction mixture was added to a saturated ammonium sulfate solution, extracted with ether and the extract washed with 10% sulfuric acid, filtered through Celite, washed with brine and dried. Evaporation of the solvent, a residue as an oil. The crude oil was treated with a mixture of 20 ml. of tetrahydrofuran, 20 ml. of water and 40 ml. of acetic acid and stirred at 25° for one hour. After evaporation of the solvent, the residue was chromatographed on silica gel. Elution with 15% ethyl acetate in hexanes afforded 2.1 g. of the first title product as an oil, $\lambda_{max}^{film}$ 2.9, 3.4, 5.69, 6.2, 6.82, 6.92, 8.6, 9.65, 10.2, 12.8, 13.5 and 14.13 μ.

NMR Analysis: δ 0.83 and 0.92

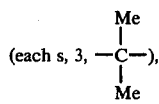

(each s, 3, —C—), 1.94 (s, 1, OH), 3.72 (s, 3, —COOCH₃), 3.87 (m, 1, 15-H), 5.44 (m, 2, 5 & 6-H), 5.83 (t, 2, 13 & 14-H) and 7.32 (s, 5, aromatic H) ppm.

Mass Spectral Analysis: M+ at m/e 412 (theory 412).

Continuing elution with 17% ethyl acetate in hexane afforded 1.4 g. of the second title product as an oil, $\lambda_{max}^{film}$ 2.85, 3.4, 5.67, 6.16, 6.80, 6.88, 7.26, 8.59, 10.18, 12.7, 13.5 and 14.1 μ.

NMR Analysis: δ 0.85 and 0.97

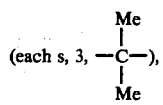

(each s, 3, —C—), 1.76 (s, OH), 3.70, (s, 3, —COOCH₃), 3.88 (M, 1, 15-H), 5.44 (m, 2, 5 & 6-H), 5.73 (m, 2, 13 & 14-H) and 7.31 (s, 5, aromatic H) ppm.

Mass Spectral Anaylsis: M+ at m/e 412 (theory 412).

EXAMPLE 7 dl-7-{2β-[(3R)-3-Hydroxy-4,4-Dimethyl-5-Phenyl-trans-1-Pentenyl]-5-Oxo-1α-Cyclopentyl}-cis-5-Heptenoic Acid VIII A solution of 1.3 g. of dl-7-{2β-[(3R)-3-hydroxy-4,4-dimethyl-5-phenyl-trans-1-pentyl]-5-oxo-1α-cyclopentyl}-cis-5-heptenoic acid, methyl ester in 20 ml. of tetrahydrofuran and 40 ml. of 2N sodium hydroxide solution was stirred at 25° for 20 hours under nitrogen. The mixture was acidified at 20° with acetic acid and extracted with ether. After washing and drying, the solvent was evaporated and the residue chromatographed on silica gel. Elution with 30% ethyl acetate afforded 1.3 g. of the title product as an oil, $\lambda_{max}^{film}$ 2.9 (shoulder), 3.4, 5.74, 6.18, 6.62, 6.82, 7.08, 8.04, 8.61, 10.2, 12.8, 13.52 and 14.15μ.

NMR Analysis: δ 0.82 and 0.90

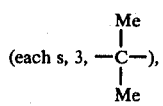

(each s, 3, —C—), 3.90 (m, 1, 15-H), 5.46 (m, 2, 5 & 6-H), 5.80 (m, 2, 13 & 14-H), 6.12 (s, 2, —OH) and 7.30 (s, 5, aromatic H) ppm.

Mass Spectral Analysis: M+ —C₁₀H₁₃ at m/e 265.1439 (theory 265.1436).

EXAMPLE 8 dl-2β-[(3R)-3-Hydroxy-4,4-Dimethyl-5-Phenyl-trans-1-Pentenyl]-5-Oxo-Cyclopentane Heptanoic Acid IX A solution of 0.60 g. of dl-{2β-[(3R)-3-hydroxy-4,4-dimethyl-5-phenyl-trans-1-pentenyl]-5-oxo-1α-cyclopentyl}-cis-5-heptenoic acid and 0.3 g. of tris(triphenylphosphine)rhodium (I) chloride in 20 ml. of a mixture of ethanol-benzene (1:1) was hydrogenated at 25° and atmospheric pressure until one equivalent of hydrogen was absorbed. The solution was evaporated and the residue chromatographed on silica gel. Elution with 25% ethyl acetate in hexane afforded 0.32 g. of the title product as an oil, $\lambda_{max}^{film}$ 2.9 (shoulder), 3.45, 5.75, 6.18, 6.62, 6.77, 7.04, 7.78, 8.58, 10.19, 12.74, 13.47 and 14.06μ.

NMR Analysis: δ 0.82 and 0.90

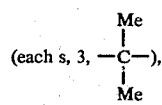

(each s, 3, —C—), 3.84 (m, 1, 15-H), 5.26 (m, 2, —OH), 5.67 (t, 2, 13 & 14-H) and 7.21 (s, 5, aromatic H) ppm.

Mass Spectral Anaylsis: M+-C₁₀H₁₃ at m/e 267.1586 (theory 267.1595).

EXAMPLE 9

In using the compounds of the invention to produce bronchodilating effects in warm-blooded animals, they may be administered in a variety of dosage forms: oral, injectable, and aerosol inhalation. Aerosol inhalation is a preferred method because of its rapid onset of action, great potency, and specificity of action. The particular dosage to obtain the bronchodilating effect will vary with the particular compound employed, the particular animal involved, and the degree of bronchodilation desired. In the guinea pig, by aerosol inhalation, the dose to produce bronchodilation is from about 0.15 micrograms to about 25 micrograms, and preferably from about 0.15 to about 15 micrograms. The bronchodilation produced upon aerosol inhalation can be observed by the method of Rosenthale et al., J. Pharmacol. Exp. Ther., 178, 541 (1971). Using this procedure the following results were obtained:

| Compound | Dose (μg) | Percent Inhibition of the bronchoconstricting effects of a standard dose* of acetylcholine |
|---|---|---|
| dl-2β-[(3R)-3-hydroxy-4,4-dimethyl-5-phenyl-trans-1-pentenyl]-5-oxo-cyclopentane heptanoic acid | 0.15 | 46 |
| | 1.50 | 66 |
| | 15 | 60 |

*The dose (i.v. of acetylcholine which produces a ca. 30% bronchoconstriction.

EXAMPLE 10

In the use of the compounds of the invention to produce hypotensive effects in warm-blooded animals, administration by the injectable route is preferred, preferably the intravenous route.

Thus in the anesthetized dog by the intravenous route the dose to produce hypotension is from about 1 μg/kg.

to about 200 μg/kg. and preferably from about 10 μg/kg. to about 100 μg/kg. Using this procedure the following results were obtained:

| Compound | Dose (μg/kg.) | Δ B.P. (mm. Hg.)* |
|---|---|---|
| dl-7-}2β-[(3R)-3-hydroxy-4,4-dimethyl-4-phenyl-trans-1-butenyl]-5-oxo-1α-cyclopentyl{-cis-5-heptenoic acid | 10 | −30 |
| dl-2β-[(3R)-3-hydroxy-4,4-dimethyl-4-phenyl-1-butyl]-5-oxo-1α-cyclopentane heptanoic acid | 10 | −14 |
|  | 100 | −26 |

*Average of two animals.

The subject matter which the Applicant regards as his invention is particularly pointed out and distinctly claimed as follows:

1. A chemical compound of the structure:

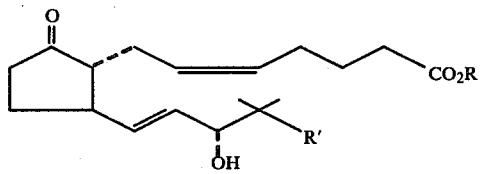

wherein R is alkyl of from 1 to 6 carbon atoms, and R¹ is phenyl.

2. A chemical compound of claim 1 wherein R is methyl.

3. A chemical compound of the structure:

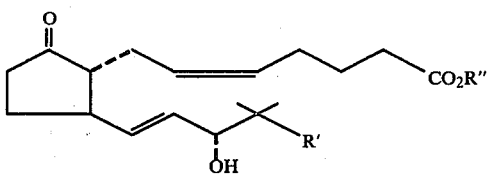

wherein R¹ is phenyl and R″ is hydrogen, an alkali metal cation, or a pharmacologically acceptable cation derived from ammonia or a basic amine.

4. The compound of claim 3 wherein R″ is hydrogen.

5. A chemical compound of the structure:

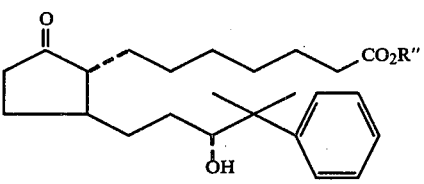

wherein R″ is hydrogen, an alkali metal cation, or a pharmacologically acceptable cation derived from ammonia or a basic amine.

6. The chemical compound of claim 5 wherein R″ is hydrogen.

* * * * *